(12) United States Patent
Wurster et al.

(10) Patent No.: US 9,061,133 B2
(45) Date of Patent: Jun. 23, 2015

(54) FOCUSED ULTRASONIC TRANSDUCER NAVIGATION SYSTEM

(71) Applicant: Brainsonix Corporation, Sherman Oaks, CA (US)

(72) Inventors: Walter William Wurster, Reno, NV (US); Michael Allen Gustafson, Virginia City, NV (US); Elaine Patrice Pelletier, Minden, NV (US); Richard Alan Waltz, Carson City, NV (US)

(73) Assignee: BRAINSONIX CORPORATION, Sherman Oaks, CA (US)

( * ) Notice: Subject to any disclaimer, the term of this patent is extended or adjusted under 35 U.S.C. 154(b) by 16 days.

(21) Appl. No.: 13/728,392

(22) Filed: Dec. 27, 2012

(65) Prior Publication Data

US 2014/0188011 A1 Jul. 3, 2014

(51) Int. Cl.
| A61H 1/00 | (2006.01) |
| A61N 7/00 | (2006.01) |
| A61N 7/02 | (2006.01) |
| A61B 8/00 | (2006.01) |
| A61B 19/00 | (2006.01) |

(52) U.S. Cl.
CPC .. *A61N 7/00* (2013.01); *A61N 7/02* (2013.01); *A61B 19/201* (2013.01); *A61N 2007/0091* (2013.01); *A61B 8/4227* (2013.01)

(58) Field of Classification Search
CPC ........ A61B 8/00; A61B 8/4272; G10K 11/00; G01S 15/00
See application file for complete search history.

(56) References Cited

U.S. PATENT DOCUMENTS

| 4,343,301 | A |   | 8/1982  | Indech |
| 5,247,935 | A |   | 9/1993  | Cline et al. |
| 5,275,165 | A |   | 1/1994  | Ettinger |
| 5,291,890 | A |   | 3/1994  | Cline |
| 5,323,779 | A |   | 6/1994  | Hardy |
| 5,381,794 | A | * | 1/1995  | Tei et al. ................... 600/459 |
| 5,409,446 | A | * | 4/1995  | Rattner ........................ 601/4 |
| 5,546,438 | A |   | 8/1996  | Hynecek |
| 5,738,625 | A |   | 4/1998  | Gluck |
| 5,752,515 | A |   | 5/1998  | Jolesz |
| 6,066,123 | A |   | 5/2000  | Li |
| 6,088,613 | A |   | 7/2000  | Unger |
| 6,094,598 | A |   | 7/2000  | Elsberry |
| 6,148,225 | A |   | 11/2000 | Kestler et al. |
| 6,198,956 | B1 |  | 3/2001  | Dunne |
| 6,198,958 | B1 |  | 3/2001  | Ives |

(Continued)

OTHER PUBLICATIONS

Yoo, et al., Focused ultrasound modulates region-specific brain activity, Elsevier Journal-NeuroImage, vol. 56, 2011, pp. 1267-1275.

(Continued)

*Primary Examiner* — Tse Chen
*Assistant Examiner* — Mark Remaly
(74) *Attorney, Agent, or Firm* — Stolowitz Ford Cowger LLP

(57) ABSTRACT

A focused ultrasonic transducer navigation system attaches to a patient and includes a housing that contains an ultrasonic device. An alignment system moves the housing, and moves the ultrasonic device within the housing, so a focal point of ultrasonic energy from the ultrasonic device is aligned in x, y, and z planes with a target location in the patient. The alignment system realigns the focal point of the ultrasonic device with the same patient target location over multiple therapy sessions eliminating repeated use of an MRI system for repeatedly realigning the ultrasonic device.

30 Claims, 9 Drawing Sheets

(56) References Cited

U.S. PATENT DOCUMENTS

| | | | |
|---|---|---|---|
| 6,261,231 B1 * | 7/2001 | Damphousse et al. | 600/437 |
| 6,267,734 B1 | 7/2001 | Ishibashi | |
| 6,348,793 B1 | 2/2002 | Balloni | |
| 6,413,216 B1 | 7/2002 | Cain et al. | |
| 6,612,988 B2 | 9/2003 | Maor | |
| 6,708,051 B1 | 3/2004 | Durousseau | |
| 7,283,861 B2 | 10/2007 | Bystritsky | |
| 7,300,414 B1 | 11/2007 | Holland et al. | |
| 7,427,265 B1 | 9/2008 | Keilman | |
| 7,505,807 B1 | 3/2009 | Kucharczyk | |
| 8,086,296 B2 | 12/2011 | Bystritsky | |
| 8,343,083 B1 * | 1/2013 | Fencel | 602/23 |
| 2002/0127230 A1 | 9/2002 | Chen | |
| 2002/0173697 A1 | 11/2002 | Lenhardt | |
| 2003/0204135 A1 | 10/2003 | Bystritsky | |
| 2004/0048795 A1 | 3/2004 | Ivanova | |
| 2005/0240126 A1 | 10/2005 | Roley | |
| 2006/0184069 A1 | 8/2006 | Vaitekunas | |
| 2007/0016031 A1 | 1/2007 | Mourad et al. | |
| 2007/0299370 A1 | 12/2007 | Bystritsky | |
| 2008/0064960 A1 * | 3/2008 | Whitmore et al. | 600/459 |
| 2008/0262350 A1 | 10/2008 | Unger | |
| 2008/0275340 A1 | 11/2008 | Beach | |
| 2009/0005711 A1 | 1/2009 | Konofagou | |
| 2009/0112133 A1 | 4/2009 | Deisseroth | |
| 2009/0318935 A1 * | 12/2009 | Sundar et al. | 606/130 |
| 2010/0010394 A1 | 1/2010 | Liu | |
| 2011/0092800 A1 | 4/2011 | Yoo | |
| 2011/0094288 A1 | 4/2011 | Medan | |
| 2011/0172653 A1 | 7/2011 | Schneider | |
| 2011/0213200 A1 | 9/2011 | Mishelevich | |
| 2012/0083719 A1 | 4/2012 | Mishelevich | |
| 2014/0188011 A1 | 7/2014 | Wurster | |

OTHER PUBLICATIONS

Mulgaonkar et al., A prototype stimulator system for noninvasive low intensity focused ultrasound delivery; Stud Health Technol Inform, vol. 173, 2012, pp. 297-303.

Min et al, Focused ultrasound-mediated suppression of chemically-induced acute epileptic EEG activity, BMC Neuroscience; 2011, 12:23, pp. 1-12.

Bystritsky et al., A review of low-intensity focused ultrasound pulsation, Elsevier Journal-Brain Stimulation, vol. 4, 2011, pp. 125-136.

Barlow, et al., The risk of seizure after receipt of whole-cell pertussis or measles, mumps, and rubella vaccine, New England journal of Medicine, vol. 345, No. 9, pp. 656-661 (2001).

Tyler, et al., Remote excitation of neuronal circuits using low-intensity, low-frequency ultrasound, PlosOne, vol. 3, Issue 10, pp. 1-11 (Oct. 2008).

Turfail, et al., Ultrasonic neuromodulation by brain stimulation with transcranial ultrasound, Nature Protocols, vol. 6, No. 9, pp. 1453-1470 (2011).

Clement et al., A hemisphere array for non-invasive brain therapy and surgery, Physics in Medicine and Biology, vol. 45, No. 12, pp. 3707-3719 (2000).

Colucci et al., Focused ultrasound effects on nerve action potential in vitro, Ultrasound in Med. & Biol., vol. 35, No. 10, pp. 1737-1747 (2009).

Tufail, et al., Transcranial Pulsed Ultrasound Stimulates Intact Brain Circuits, Neuron, vol. 66, pp. 681-694 (Jun. 10, 2010).

Yang, et al., Transcranial focused ultrasound to the thalamus is associated with reduced extracellular GABA levels in rats, Neruopsychobiology, vol. 65, pp. 153-160 (2012).

Yoo, et al., Transcranial focused ultrasound to the thalamus alters anesthesia time in rats, Neuroreport, vol. 22(15), pp. 783-787 (Oct. 26, 2011).

Hameroff, et al., Transcranial ultrasound (TUS) effects on mental states: a pilot study, Brain Stimulation, vol. 6, pp. 409-415 (2013).

Korb, et al., Low-intensity focused ultrasound pulstation device used druing magnetic resonance imaging: evaluation of magnetic resonance imagin-related heating at 3 tesla/128MHz, Neuromodulation, (2013).

Bystritsky et al., a preliminary study of fMRi-guided rTMS in the treatment of generalized anxiety disorder, J Clin Psychiatry, vol. 69, pp. 1092-1098 (Jul. 7, 2008).

Deffieux et al., Low-intensity focused ultrasound modulates monkey visuomotor behaviour, Current Biology, vol. 23, pp. 2430-2433 (Dec. 2, 2013).

Mehic et al., Increased anatomical specificity of neuromodulation via modulated focused ultrasound, Plos One, vol. 9, Issue 2, pp. 1-13 (Feb. 2014).

Kim et al., Estimation of the spatial profile of neuromodulaton na dthe temporal latency in motor responses induced by focused ultrasound brain stimulation, Neurophysiology Neuroreport, vol. 25, No. 7., pp. 475-479 (2014).

Metwally, et al., Influence of the anitsotropic mechanical properties of the skull in low-intensity focused ultrsound towards neuromodulation of the brain, 35th Ann Int Conf of IEEE EMBS, Osaka, Japan pp. 4565-4568 (Jul. 3-7, 2013).

Winhye, et al., Creation on various skiin sensations using pulsed focused ultrasound: evidence for functional neuromodulation, Internation Journal of Imaging Ssytems and Technology, (Dec. 27, 2013).

Tyler et al., Remote excitation of neuronal circuits using low intensity, low frequency ultrasound, Ultrasonic Neurostimulation, vol. 3, No. 10, pp. 1-11 (2008).

Tyler, W.J., Noninvasive Neuromodulation with Ultrasound? a continuum mechanics hypothesis, pp. 1-12 (2010).

* cited by examiner

FOCUSED ULTRASONIC TRANSDUCER NAVIGATION SYSTEM

BACKGROUND

Ultrasonic energy is used to treat different medical conditions. During treatment, transducers apply ultrasonic energy to a treatment zone or "target" within a patient. For example, the ultrasonic energy may be applied to a clot to dissolve or remove a blockage within the brain. Of course other types of disorders also may be treated with ultrasonic energy. For example, ultrasonic therapy may be used for treating other psychiatric, neurological, and medical disorders.

Ultrasonic therapy may involve applying ultrasonic energy to the same treatment zone over multiple treatment sessions. Each treatment session needs to apply the ultrasonic accurately and repeatedly to the same treatment zone. A Magnetic Resonance Imaging (MRI) machine may first scan the brain, or other body part, to locate the target area. The ultrasonic system is then adjusted to focus the ultrasonic energy onto the located target area. Ultrasonic therapy may be time consuming and expensive since each session requires a trip to a hospital and use of a MRI machine to relocate the same target area.

DETAILED DESCRIPTION

Figure 1A:
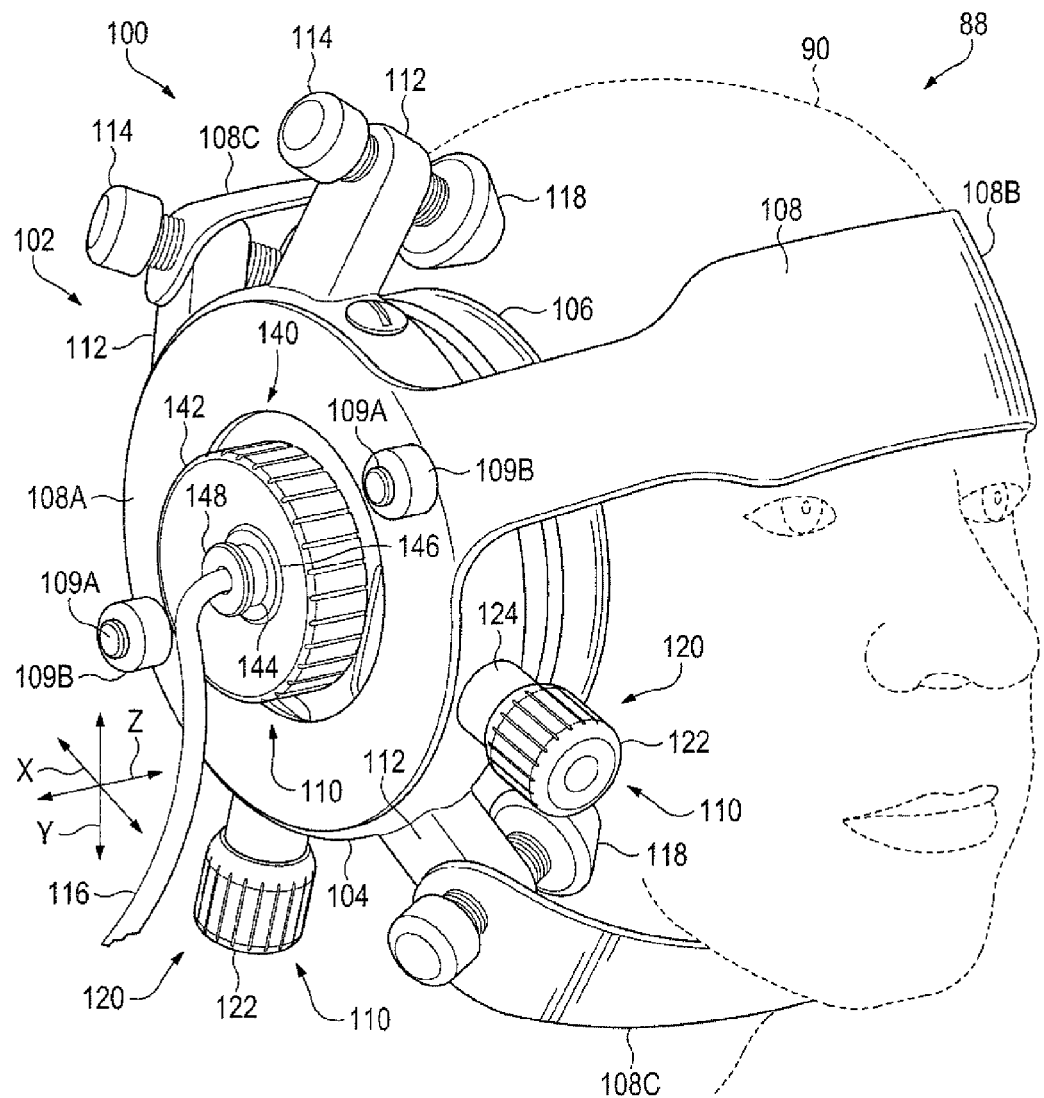
FIG. 1A is a perspective view of a focused ultrasonic transducer navigation system.

FIG. 1A shows a perspective view of a focused ultrasonic Transducer Navigation System (TNS) 100. TNS 100 may be attached to a patient 88 and may apply ultrasonic energy to precise target locations within patient 88. The explanation below discusses the specific example of using TNS 100 to apply ultrasonic energy to a target location within head 90 of patient 88. However, it should be understood that TNS 100 may apply any type of sonic, magnetic, or any other alternative energy to any target location within any body part of patient 88. TNS 100 may be used on human patients or animal patients.

A housing assembly 102 comprises an outer housing 104 attached to a movable inner housing 106. A transducer (see FIG. 4) may be located within inner housing 106. A power cable 116 may attach to the transducer and extend up through inner housing 106 and outer housing 104.

A first vertical strap 108C attaches to elevating screws 114 and wraps around the top of head 90 and underneath the chin of patient 88. A second horizontal strap 108 includes a ring shaped section 108A that attaches to an outside surface of outer housing 104 via screws 109A and nuts 109B and a headband section 108B that wraps around the front over the eyes and back of head 90. While shown attached to head 90, it should be understood that straps 108, or other attachment devices, may attach housing assembly 102 to other body parts of patient 88. The housing assembly 102 may be attached by straps 108 to the right side or left side of head 90 to apply ultrasonic energy to targets on inside either side of head 90.

Three housing arms 112 may extend radially out from sides of outer housing 104. Elevating screws 114 may rotatably extend through housing arms 112 and may include elastomeric cushions 118 that press up against head 90. Elevating screws 114 may be rotated downward pressing against head 90 to reduce some of the compressive force of inner housing 106 against head 90. This will be described in more detail below.

An alignment system 110 may move the transducer within inner housing 106 into different x, y, and/or z positions with respect to head 90. The x position may refer generally to front to back positions with respect to head 90, the y position may refer generally to top to bottom positions with respect to head 90, and the z position may refer generally to a transverse inside to outside, or left to right positions, with respect to head 90.

If TNS 100 were attached on the top of head 90, the x position may refer to front to back positions with respect to head 90, the y position may refer to the left to right or side to side positions with respect to head 90, and the z position may refer to the transverse inside to outward or top to bottom positions with respect to head 90.

Alignment system 110 may comprise side adjustment assemblies 120 and a top adjustment assembly 140 that have the unique ability to move the transducer within inner housing 106 in different x, y, and z directions while TNS 100 remains attached to head 90 of patient 88. This allows more precise alignment of the transducer with a target location within head 90. Alignment system 110 also may provide quicker and more accurate reattachment of the TNS to head 90 to a same relative position with respect to the target location. This allows TNS 100 to be repeatedly reattached during multiple ultrasonic therapy sessions without using a MRI device to relocate the target location.

Side adjustment assemblies 120 each include a side adjustment knob 122 that rotatably attaches to a side extension 124 that extends radial out from the side of outer housing 104. Top adjustment assembly 140 includes a top adjustment knob 142 that is rotatably attached to outer housing 104. A threaded ring 146 extends out through the middle of top adjustment knob 142. A top end 144 of a transducer lid extends out through threaded ring 146 and a cap 148 inserts into a center cavity of the top end 144 of the transducer lid. Cap 148 operates as a wire guide for receiving cable 116 and also operates as a stop for top end 144 of the transducer lid.

Figure 1B:
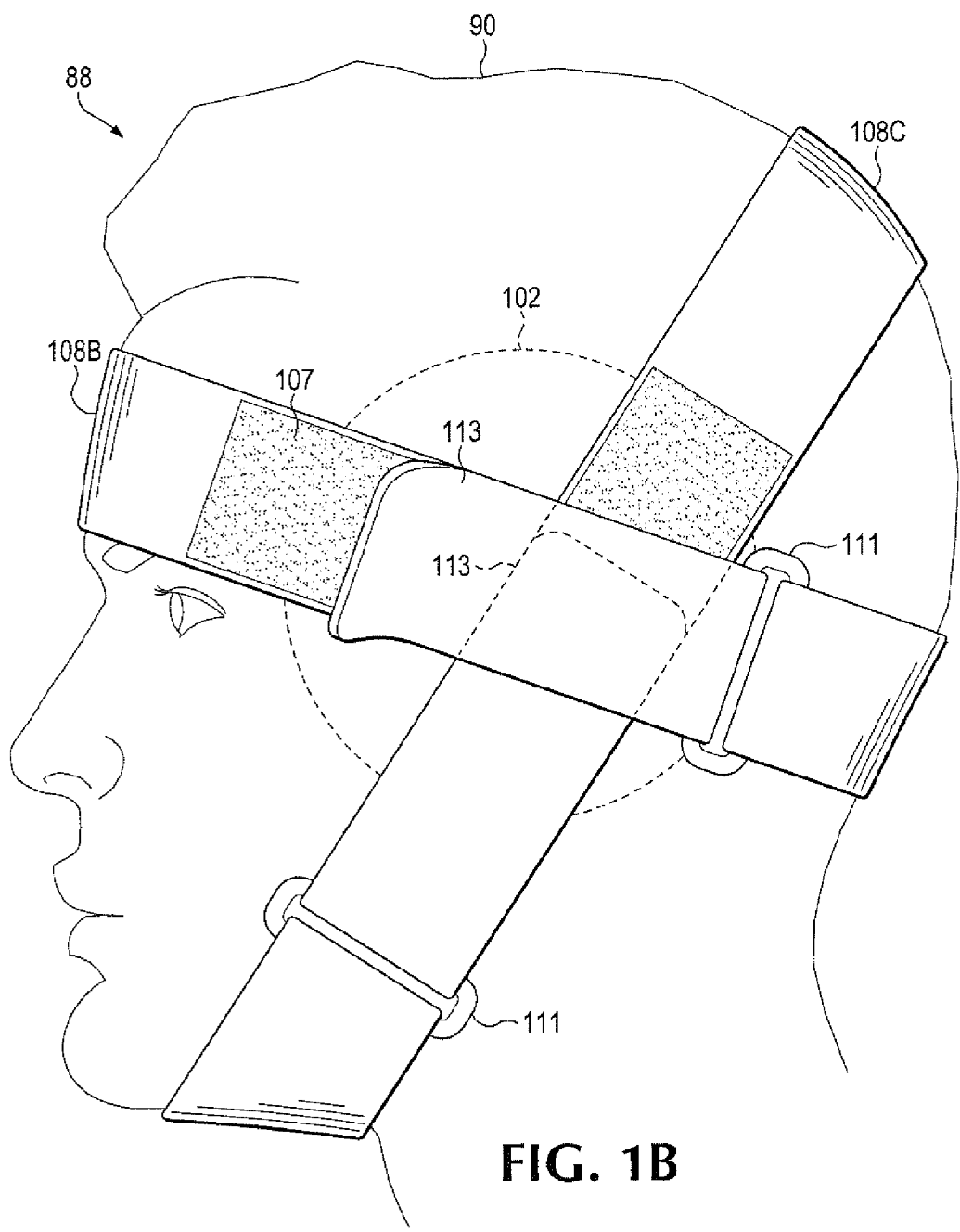
FIG. 1B is a side view of straps used for attaching the ultrasonic transducer navigation system to a patient.

FIG. 1B shows opposite ends 113 of strap sections 108B and 108C. In one example, a hook and eye type material 107, such as Velcro®, may be attached to the ends of strap 108. For example, ends 113 of straps 108 may include a hook material and may be fed through cinches 111. Strap ends 113 are pulled to hold housing assembly 102 snugly against the opposite side of head 90. The hook material on strap ends 113 is then attached to eye material 107.

Other attachment assemblies may be used for attaching ends 113 of straps 108. For example, hook and eye buckles or ratchet buckles may be used on ends 113 of straps 108. In yet another example, strap sections 108B and 108C may be formed from elastic materials that are stretched and held compressively over head 90. Of course other attachment devices also may be used.

In one example, straps 108 may be made out of leather. However, any material may be used that can securely hold housing assembly 102 against patient 88. As just discussed, straps 108 may alternatively be an elastic plastic, rubber, or cloth material. Straps 108 may be available in multiple lengths and sizes to attach to various patient head sizes and patient body parts for small children to large adults.

Figure 2:
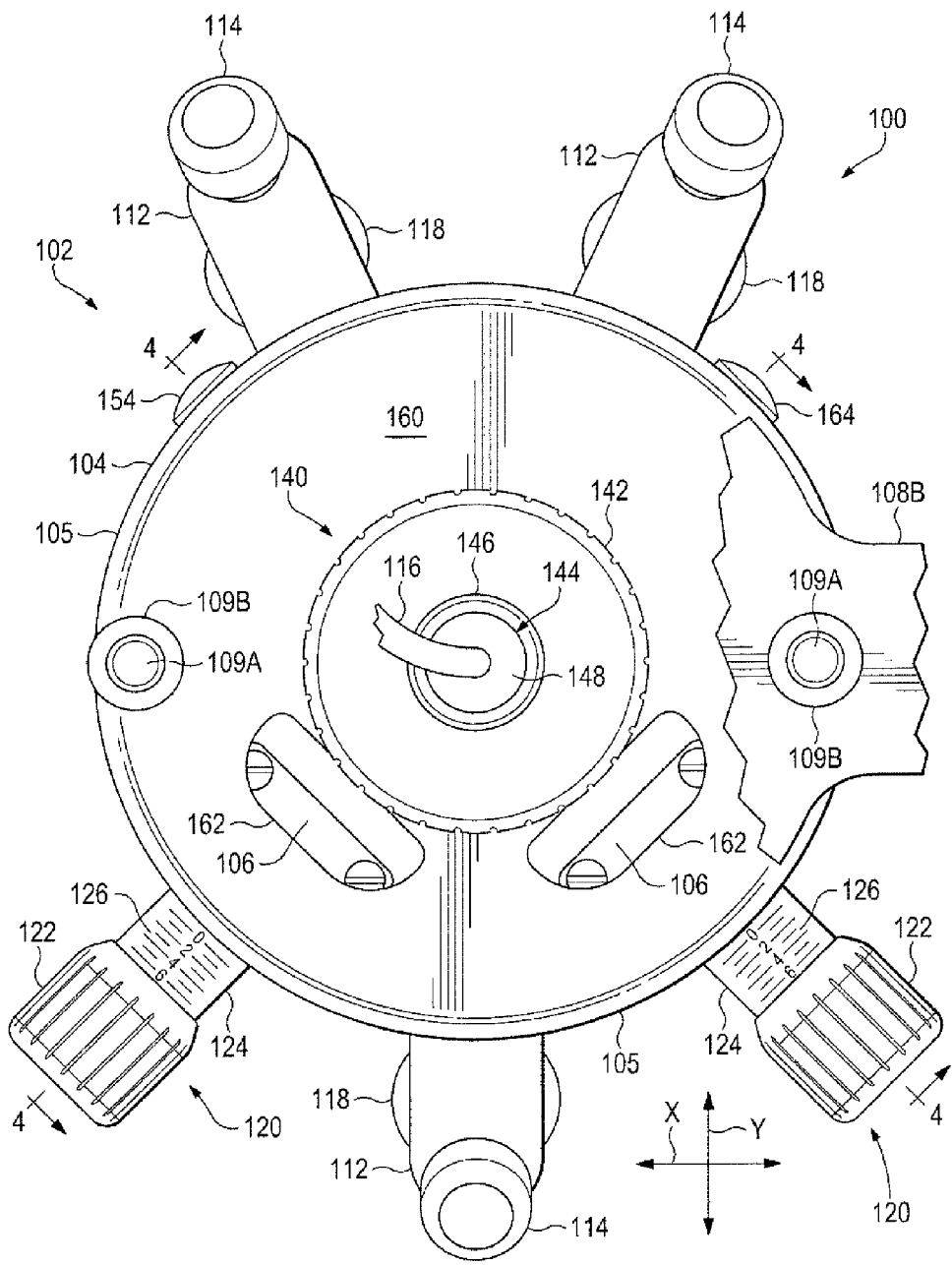
FIG. 2 is a side view of the ultrasonic transducer navigation system.

FIG. 2 shows a side view of TNS 100. Outer housing 104 comprises a circular outside surface 160 with two openings 162 that show a portion of inner housing 106 attached to side adjustment assemblies 120. Housing arms 112 extend radially out from the sides of outer housing 104 and operate similar to a tri-pod allowing TNS 100 to be steadily supported by elevating screws 114 on varying elevational locations on head 90.

Side adjustment assemblies 120 may each include inner adjustment screws (see FIG. 4) that have first ends that attach to inner housing 106 and second ends that attach to side adjustment knobs 122. Two threaded stationary pins 164 are located on sides of outer housing 104 opposite adjustment assemblies 120. Pins 164 slidingly insert into sides of inner housing 106 opposite the sides attached to side adjustment assemblies 120.

Side adjustment knobs 122 can be rotated in both clockwise and counterclockwise directions. For example, rotating either one of side adjustment knobs 122 in a clockwise direction may cause the inner adjustment screw to rotate inward. The inner adjustment screw in turn moves inner housing 106 away from side adjustment assembly 120 and toward an opposite end of outer housing 104 and toward one of pins 164. Rotating one of side adjustment knobs 122 also causes knob 122 to move radially inward over an outside surface of side extension 124 and toward an outside perimeter 105 of outer housing 104.

Rotating any combination of side adjustment knobs 122 in an opposite counter clockwise direction may cause the inner adjustment screws to rotate outward. The inner adjustment screw in turn may pull inner housing 106 toward side adjustment assembly 120 and away from the opposite end of outer housing 104 where pin 164 is located. The counter clockwise rotation also may cause side adjustment knob 122 to move radially outward over the outside surface of side extension 124 away from outside perimeter 105 of outer housing 104.

Gradations 126 are imprinted on the outside surface of side extensions 124. In one example, each gradation 126 may be spaced apart one millimeter (mm). Gradations 126 in combination with side adjustment knobs 122 operate as micrometers identifying distances of x and y movement of the transducer contained inside of inner housing 106. For example, after TNS 100 is attached to the head of the patient, side adjustment knobs 122 may be rotated to adjust the location of the transducer so a focal point of ultrasonic energy is directed precisely over a target area inside of the brain of the patient.

Top adjustment knob 142 is co-centrically positioned on top of outer housing 104. Threaded ring 146 is concentrically positioned within top adjustment knob 142 and cap 148 is concentrically positioned within top end 144 of the transducer lid and over threaded ring 146. Rotating top adjustment knob 142 in a first direction may move top end 144 of the transducer lid in an upward z direction away from the head of the patient. Rotating top adjustment knob 142 in a second opposite direction may move top end 144 of the transducer lid in a downward z direction toward the head of the patient.

Figure 3:
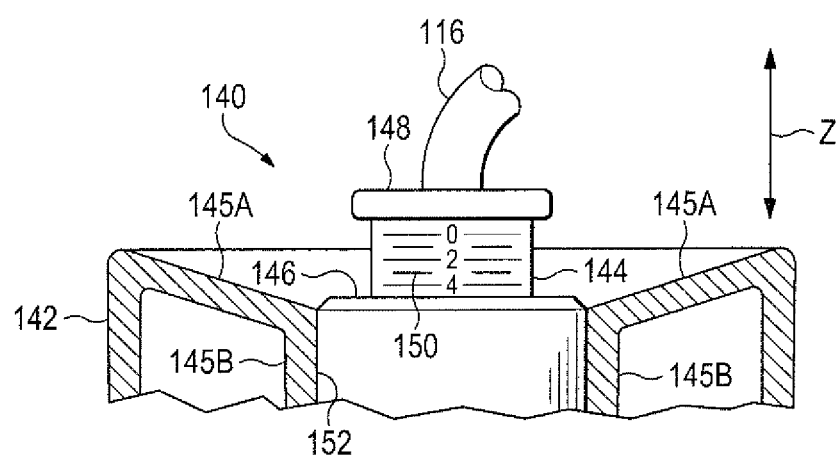
FIG. 3 is a partial side sectional view of a top adjustment assembly.

FIG. 3 shows a partial side cut away view of top adjustment assembly 140. Top adjustment knob 142 has an oppositely inclining top wall 145A and an inner side wall 145B that form an inner hole 152 that receives threaded ring 146. Screws (not shown) may insert into side walls 145B and rigidly couple adjustment knob 142 to threaded ring 146.

Rotating top adjustment knob 142 in the first direction also rotates threaded ring 146 causing top end 144 of the transducer lid to move in an upward z-direction away from the head of the patient. Rotating top adjustment knob 142 in the second opposite direction also rotates threaded ring 146 in the same direction moving top end 144 of the transducer lid in a downward z-direction toward the head of the patient.

Gradations 150 may be imprinted on an outside surface of top end 144 of the transducer lid. In one example, gradations 150 also have one millimeter spacing. Gradations 150 in relation to the location of rotating knob 142 also operate as a micrometer identifying an amount of movement of the transducer in the z direction.

Figure 4:
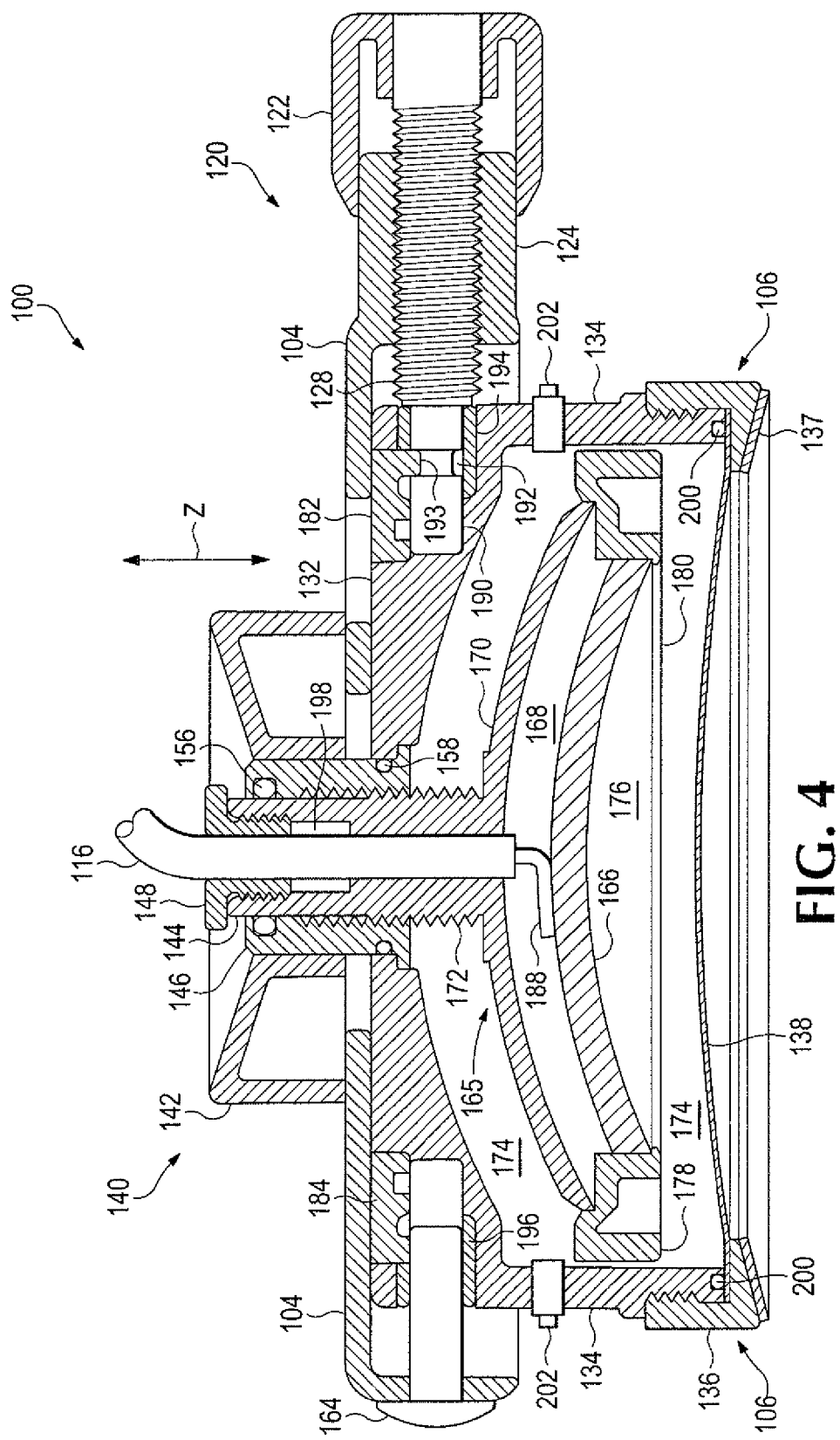
FIG. 4 is a front sectional view of the ultrasonic transducer navigation system.

FIG. 4 shows a front sectional view of TNS 100. Inner housing 106 comprises a top wall 132, side walls 134, a membrane clamping ring 136, and a hypo-allergenic flexible membrane 138 that together form a sealed inner housing chamber 174 configured to retain a transducer assembly 165. In one example, chamber 174 may be sealed and filled with degassed oil or water to improve efficiency of transferring the ultrasound waves through the skull and brain and into the target location.

Membrane 138 may be formed of a plastic or rubber material and is configured to elastically press up against the head of the patient. The threaded connection of clamping ring 136 to side walls 134 allow membrane 138 to be detached from the rest of inner housing 106. A cushion 137 may be glued to the bottom of clamping ring to increase comfort and conform around irregularities on the surface of the head of the patient. After completing the ultrasonic therapy sessions for a patient, membrane 138 may be removed and replaced with a new membrane for a next patient. A layer of gel may be spread over an outside surface of elastic membrane 138 and may maintain a continuous seal between membrane 138 and the head of the patient as will be discussed in more detail below in FIG. 8.

Transducer assembly 165 comprises a transducer 166 located between a transducer lid 170 and a transducer base 178. A space between transducer 166 and transducer lid 170 forms an airtight sealed back cavity 168. A space between transducer 166 and transducer base 178 forms a sealed front cavity 176 configured to retain water. A single transducer 166 is shown in FIG. 4. However, inner housing 106 and transducer assembly 165 may be configured to retain any transducer shape and any number of transducers, such as circular transducers and multi-transducer arrays.

Transducer lid 170 includes a neck 172 that extends up inner housing 106, outer housing 104, and threaded ring 146. As shown above, top end 144 of transducer lid 170 extends up through a top end of threaded ring 146 and includes a threaded internal hole 198 configured to threadedly receive cap 148. Left hand threads may be formed on the outside surface of cap 148 to prevent cap 148 from being unscrewed if it bottoms out against the top of ring 146. A threaded outside surface of neck 172 is configured to threadedly engage with a threaded inside surface of ring 146. Cable 116 extends through a hole in the center of neck 172 and wires from cable 116 are coupled to transducer 166.

As mentioned above, rotation of top adjustment knob 142 in a first direction rotates threaded ring 146 around threaded neck 172 moving transducer assembly 165 in a first upward z direction toward top wall 132 of inner housing 106. Rotation of top adjustment knob 142 in the opposite direction rotates threaded ring 146 around threaded neck 172 in the opposite direction moving transducer assembly 165 in a second downward z direction toward membrane 138. Cap 148 operates as a stop preventing top end 144 of transducer lid 170 from moving down below a top end of threaded ring 146.

An O-ring 156 is located between threaded ring 146 and top end 144 of transducer lid 170. An O-ring 158 is located between threaded ring 146 and the inside surface of a hole formed in top wall 132 of inner housing 106. O-rings 156 and 158 are configured to maintain a watertight or oil tight seal within chamber 174 while threaded ring 146 is rotated around transducer neck 172. An O-ring 200 may be located between the bottom end of side walls 134 and membrane clamping ring 136 to provide a watertight or oil tight seal along the bottom end of cavity 174.

Inner housing 106 may be made of a clear see-thru plastic that allows a technician to visually detect any air bubbles that may exist in the oil or water within chamber 174. Two compression nozzles 202 may be mounted within side walls 134 of inner housing 106. Compression nozzles 202 may be used for filling chamber 174 with water or oil and bleeding air bubbles out of chamber 174, similar to bleeding air out of vehicle braking systems. For example, water may be forced into a first one of nozzles 202. A second one of nozzles 202 may be depressed or unscrewed to bleed water and air bubbles from chamber 174. An indication that most or all of the air bubbles are removed may be provided when only water bleeds out of second nozzle 202. Inner housing 106 may be shaken during the bleeding process to promote the air bubbles to exit out of second nozzle 202.

Each side adjustment assembly 120 may include an inner adjustment screw 128 that forms a head 190 at a front end and is attached to a side adjustment knob 122 at a back end. A sleeve 194 is inserted into a hole formed in the side of inner housing 106. Screw head 190 inserts and rotates inside of sleeve 194. An alignment guide 182 is attached to inner housing 106 and includes a lip 193 that seats into a groove 192 formed in screw head 190. A sleeve 196 inserts into a hole formed in an outer opposite side of inner housing 106. A front end of threaded stationary pin 164 slidingly inserts into sleeve 196 and a back end of pin 164 threaded and rigidly attaches to outer housing 104. An alignment guide 184 attaches to inner housing 106 and slidingly presses against a top side of the front end of pin 164.

Threads are formed on an inside surface of a hole formed inside of each side extension 124 and engage with threads on screw 128. Rotating side adjustment knob 122 in a first direction rotates screw 128 and moves head 190 in a forward direction. Screw head 190 pushes inner housing 106 away from side extension 124 toward the opposite side of outer housing 104 while sleeve 192 on the opposite end of inner housing 106 slides further over the front end of pin 164.

Rotating side adjustment knob 122 and screw 128 in an opposite direction move head 190 in a reverse direction. Head 190 pulls lip 193 and attached inner housing 106 toward side extension 124 while sleeve 196 on the opposite side of inner housing 106 moves further out from the front end of pin 164.

Alignment guides 182 and 184 allow inner housing 106 to move into any x and y position. For example, adjustment screws 128 may move inner housing 106 into different positions. Alignment guides 182 may slide over groves 192 on screw heads 190 and alignment guides 184 may slide over pins 164 allowing movement of inner housing 106 into any x and y position within outer housing 104.

Operation Overview

Referring to FIGS. 1-4, patient 88 may have focused ultrasonic transducer navigation system (TNS) 100 strapped onto head 90 while undergoing an MRI-assisted positioning procedure. An administrator controlling an electronic power source stimulator may be in a nearby room which is safe from the magnetic field produced by the MRI device. The administrator may use a functional MRI (fMRI) method that shows images from inside of the brain of patient 88 and shows a target spot specific for treatment of a particular disorder.

TNS 100 may send a Low Intensity Focused Ultrasound Pulse (LIFUP) into the brain which can be seen and recorded on an fMRI console screen as a change in a BOLD signal. The resulting location of the ultrasonic pulse is measured relative to the spot targeted for treatment. Alternatively, the location may be verified by fMRI sequences that measure small temperature changes within the brain occurring as a result of the LIFUP stimuli.

The administrator slides patient 88 out from under the MRI device and adjusts side adjustment knobs 122 and top adjustment knob 142 (micrometer dials) to move the focus of the LIFUP generated by transducer 166 to the desired target location. The MRI comparison procedure is repeated until transducer 166 generates an ultrasonic pulse directly on the center of the target location in all three x, y, and z planes. TNS 100 is then used to perform an ultrasonic treatment.

A medically approved pen is used to mark a portion of a circle around the perimeter of inner movable housing 106 and on the head of patient 88. In one example, inner housing 106 may be made from a clear plastic material. Marking the head with the ink pen enables subsequent treatments to be administered in the office of a doctor or technician without having to use an expensive MRI device to repeatedly realign TNS 100. Thus the time and cost per treatment may be significantly reduced.

The three elevating screws 114 may be adjusted to any size and shape of head 90 and in one example may use comfortable STERalloy Elastomeric cushions 118. Elevating screws 114 raise membrane 138 slightly off head 90 to facilitate the free movement of inner moveable housing 106 in the x and y planes. Side adjustment assemblies 120 may be used to align inner housing 106 with the circle previously marked on the head of patient 88 centering ultrasonic energy generated by transducer 166 into the center of the target within the brain.

When the x and y planes are on target, elevating screws 114 are backed off to lower membrane 138 more firmly against head 90. A gel may be applied to membrane 138. The gel may maintain a contact layer between membrane 138 and head 90 while membrane 138 is moved to different x and y positions. The gel layer may prevent an air gap from forming between membrane 138 and head 90 that could reduce efficiency of the focused ultrasound waves output by transducer 166.

After completion of the LIFUP treatments, the STERalloy elastomeric cushions 118, membrane clamping ring 136 and membrane 138 may be replaced. This may prevent allergies or other undesirable effects from being transferred to other patients. The LIFUP procedure may be welcomed by the insurance companies as compared to surgery which may be more expensive and higher risk.

Initial Alignment and Treatment

During the initial MRI alignment procedure described above, the focal point of ultrasonic energy output from transducer 166 is aligned as closely as possible to the center of the target location. This allows more tolerance when realigning TNS 100 during subsequent treatments.

Figure 5:
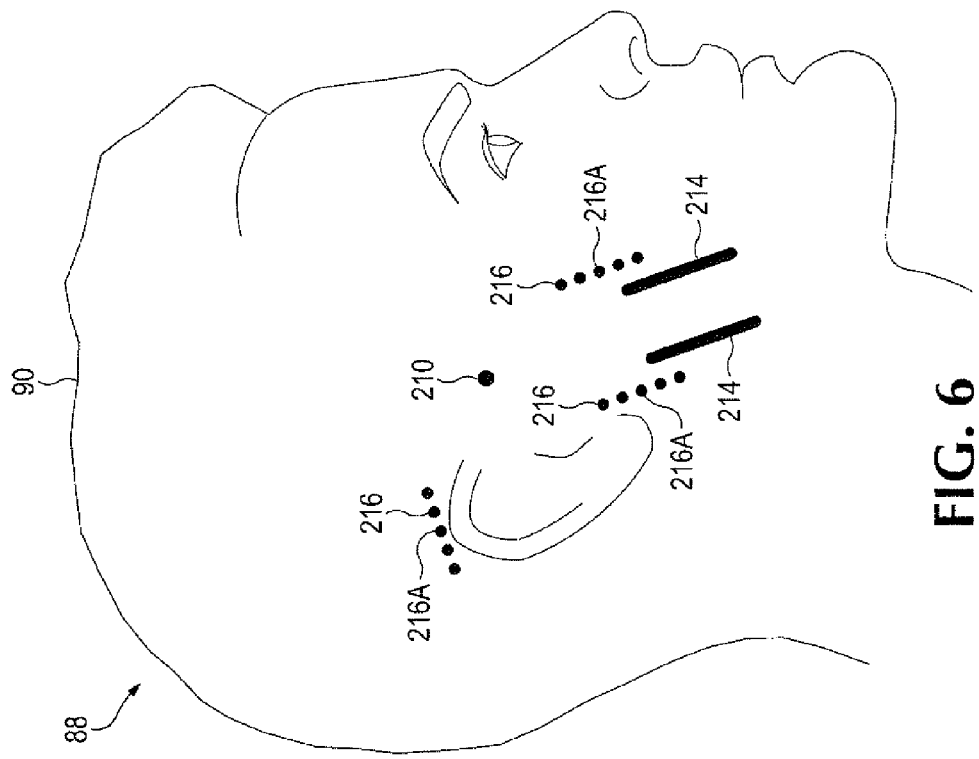
FIG. 5 is a side view of a template used for aligning the ultrasonic transducer navigation system.
Figure 6:
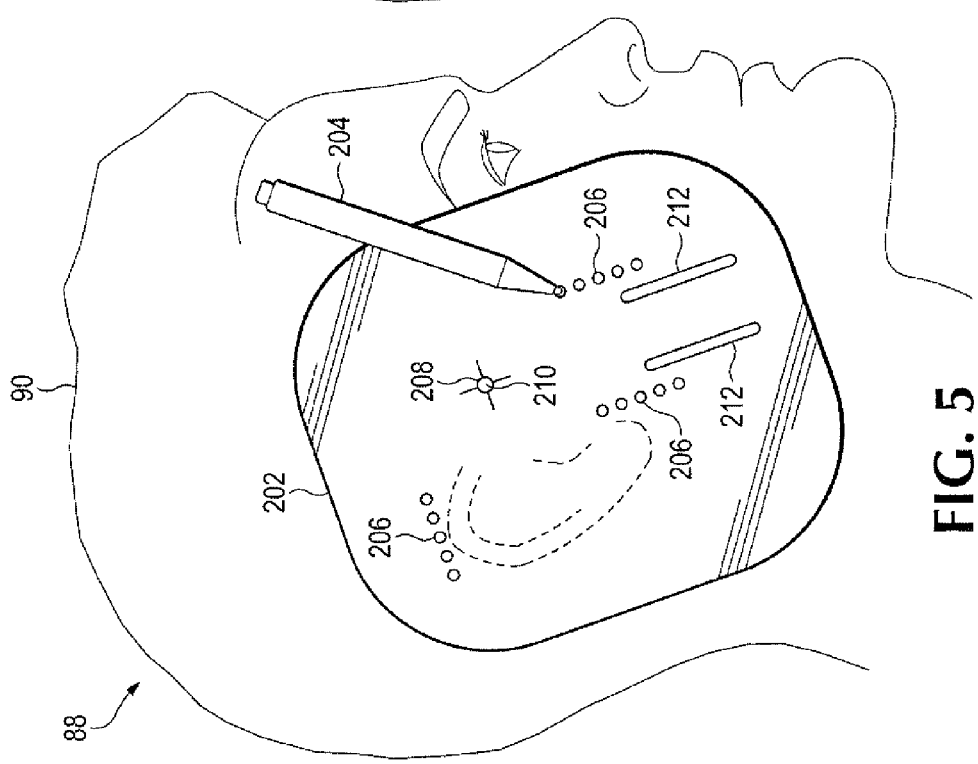
FIG. 6 shows reference marks created using the template of FIG. 5.

Referring to FIGS. 5 and 6, patient 88 may lie on their side and head 90 may be shaved in the installation location for TNS 100. A target mark 210 is applied to head 90 with an ink pen 204. A template 202 includes a hole 208 that is aligned over target mark 210, holes 206 that are aligned with the outside perimeter of inner housing 106, and two slots 212 that are aligned with one of housing arms 112. Template 202 may be made from a clear semi-rigid plastic material.

Template 202 is placed against head 90 so hole 208 aligns over target mark 210 and slots 212 are located in a desired location for one of housing arms 112. While holding template against head 90, ink pen 204 is used to apply reference lines 214 to head 90 through slots 212 and apply reference marks 216 to head 90 through holes 206. Template 202 is then removed. The third middle reference mark in each column of five reference marks 216 is alternatively referred to as a center reference mark 216A.

Figure 7:
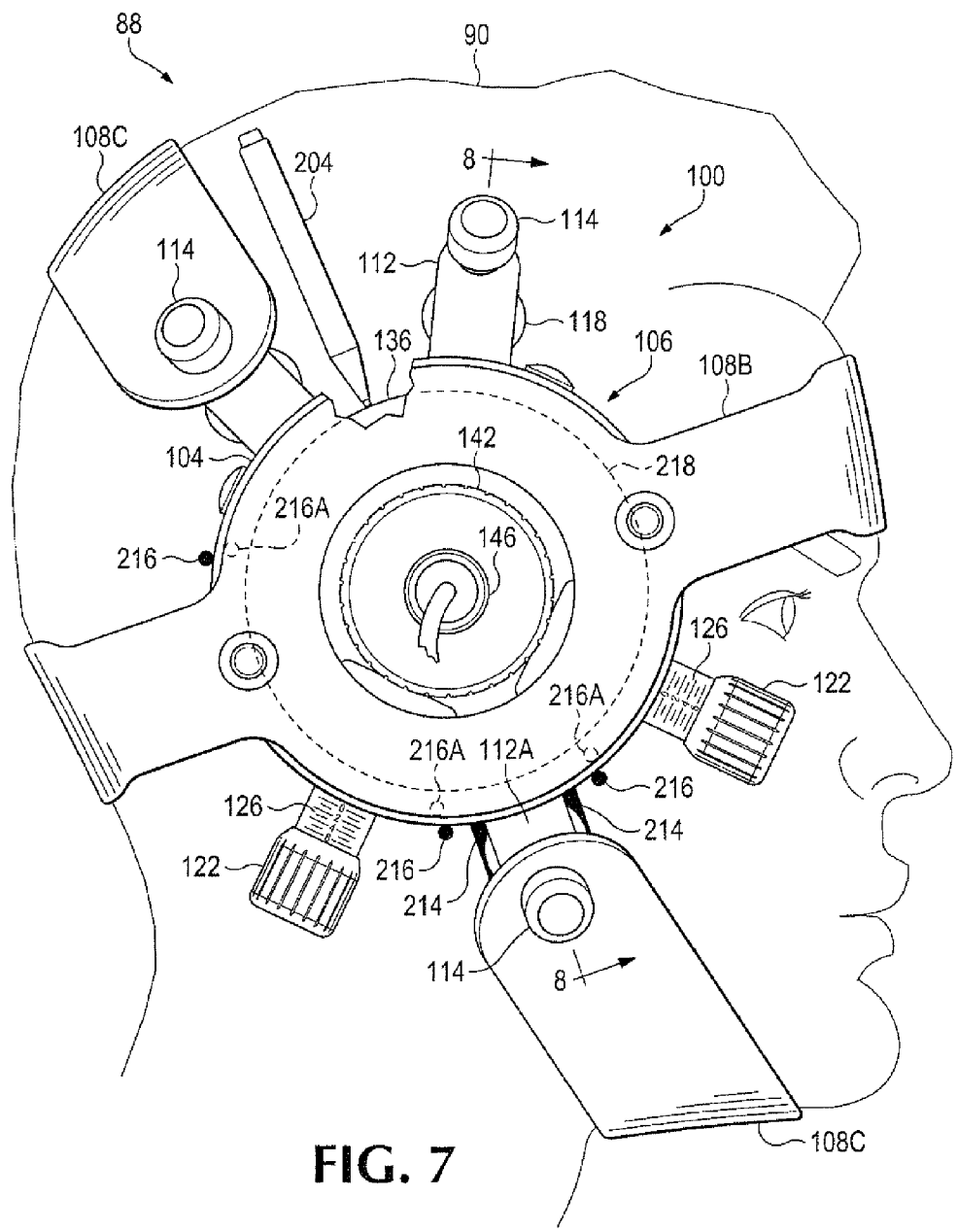
FIG. 7 is a side view of the ultrasonic transducer navigation system attached to a patient.
Figure 8:
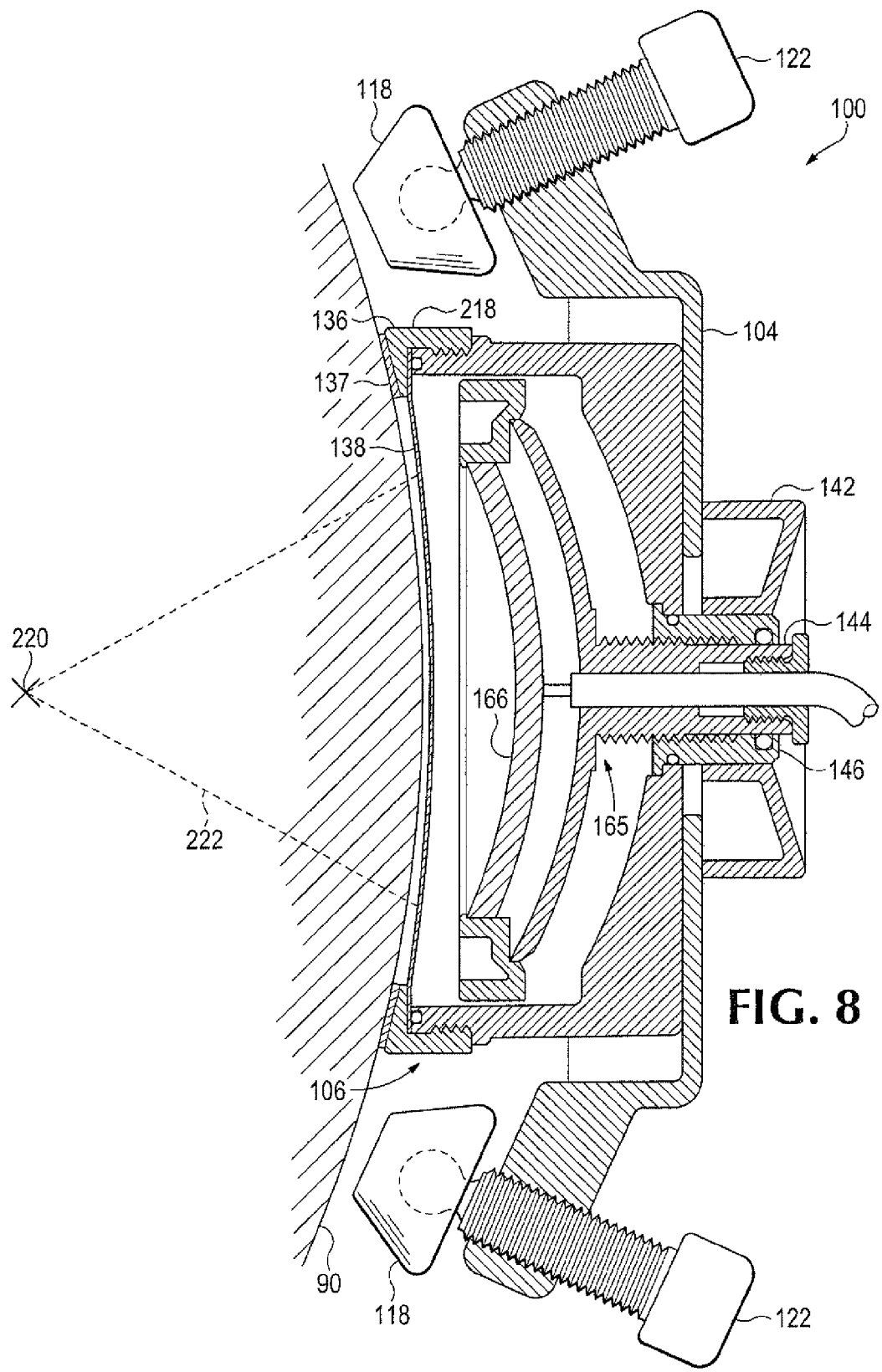
FIG. 8 is a front sectional view of the ultrasonic transducer navigation system shown in a lowered position.
Figure 9:
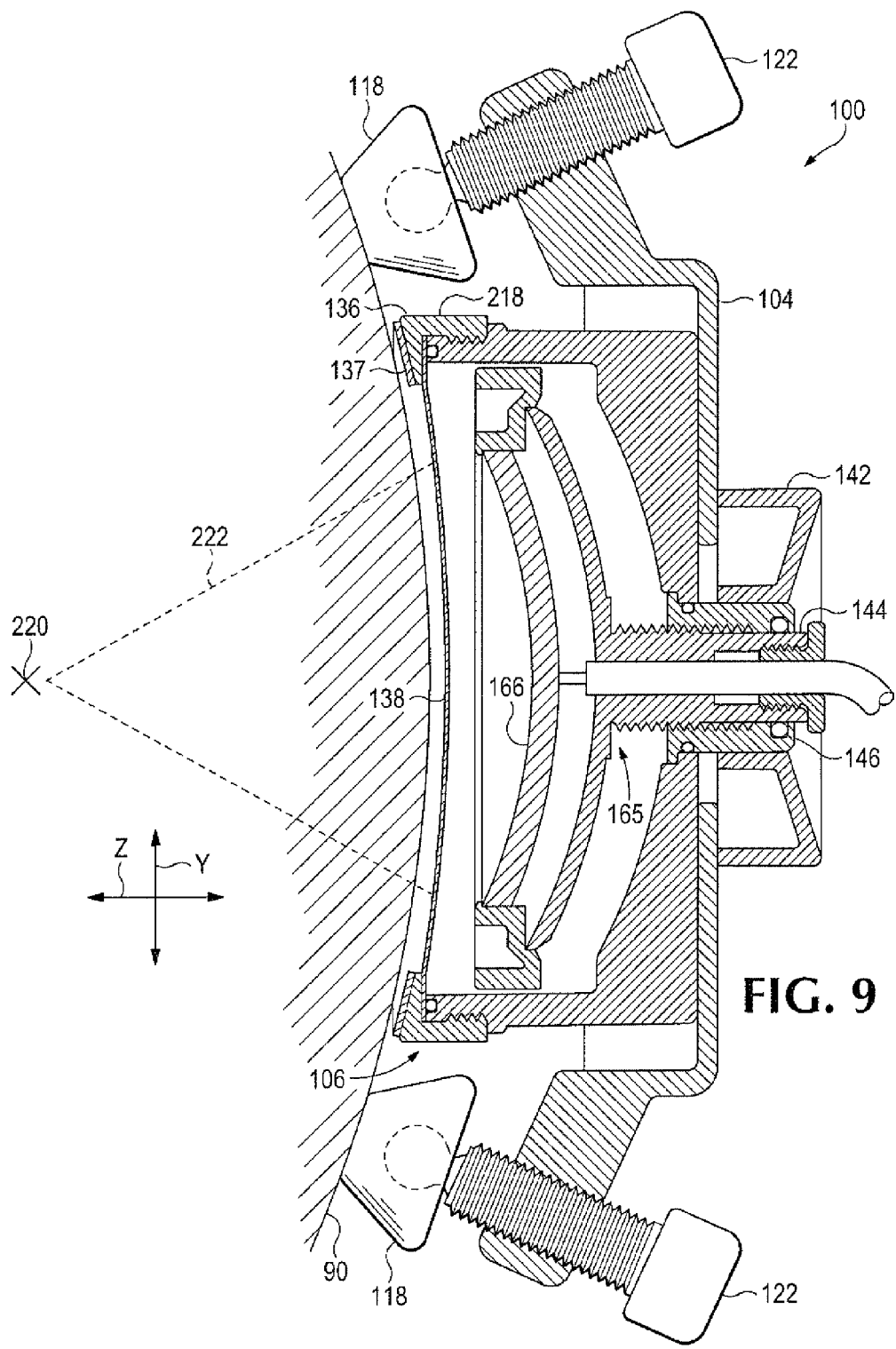
FIG. 9 is a front sectional view of the ultrasonic transducer navigation system shown in a raised position.

FIG. 7 shows a side view of TSN 100 and FIGS. 8 and 9 show front sectional views of TNS 100. FIGS. 7, 8, and 9 shows in more detail how inner housing 106 may be moved into different x, y, and z locations to align with a target location 220.

The x, y and z planes in TNS 100 may be set to nominal positions by setting side adjustment knobs 122 and top adjustment knob 142 each to 6 mm. Gel may be applied to the entire surface of membrane 138 and may be applied so it does not exceed a perimeter 218 of inner housing 106. Perimeter 218 may comprise the outside perimeter of membrane clamping ring 136.

Elevating screws 114 are raised as shown in FIG. 8 so membrane 138 contacts head 90. TNS 100 is aligned on head 90 so center reference marks 216A for each column of five reference marks 216 align with perimeter 218 as shown in FIG. 7. Housing arm 112A is aligned between reference lines 214 as shown in FIG. 7. TNS 100 is held firmly against head 90 to prevent movement and the ends of straps 108 are tightened holding TNS 100 firmly against head 90.

Patient 88 is placed under the MRI device. A pulse 222 from transducer 166 is transmitted into head 90 of patient 88 using the stimulator. The MRI device identifies the pulse location relative to target location 220 in the x and y planes. If the pulse location is off more than 6 mm in the x or y planes, TNS 100 may be removed from head 90 and the three columns of five reference marks 216 used as a guide to realign TNS 100.

For example, reference marks 216 in each column may be spaced a known distance apart. Perimeter 218 of inner housing 106 may be aligned next to a different set of reference marks 216 based on the identified distance between the focal point of ultrasonic pulse 222 and target location 220. Patient 88 then may be placed back under the MRI device and the distance re-measured between the new focal point for the ultrasonic pulse 222 and target location 220. The realignment procedure is repeated until the distance between ultrasonic pulse 222 and target location 220 is less than 6 mm in both the x and y planes.

If the x and y locations of ultrasonic pulse 222 are both within 6 mm of target location 220, elevating screws 114 are screwed down as shown in FIG. 9 to raise inner housing 106 slightly off of head 90. Side adjustment knobs 122 shown in FIG. 7 then may move inner housing 106 inside of outer housing 104. The x and y positions of inner housing 106 are adjusted based on the previously measured distance between the ultrasonic pulse 222 and target location 220.

For example, the MRI device may determine ultrasonic pulse 222 is spaced a distance of 2 mms from target location 220 in an x direction. One of side adjustment knobs 122 may be used to move inner housing 106 2 mms in the x direction. The three elevating screws 122 then may be retracted upward again as shown in FIG. 8 so membrane 138 presses firmly back against head 90. Another ultrasonic pulse 222 is applied to patient 88 and the x and y position of the new pulse measured in relation to target location 220.

The z plane position of inner housing 106 may be adjusted after the x and y positions of ultrasonic pulse 222 are aligned on target location 220. For example, a distance of ultrasonic pulse 222 from target location 220 in the z direction is measured from the MRI images. Top adjustment knob 142 is rotated to move transducer assembly 165 up or down by the measured z distance. Head 90 of patient 88 is then rescanned by the MRI device and the new location of ultrasonic pulse 222 is compared with target location 220. The measurement and adjustment process is repeated until the focal point of ultrasonic pulse 222 aligns over target location 220 in the x, y, and z planes. After alignment of ultrasonic pulse 222, TNS 100 may be checked to see if any gel is visible around perimeter 218 of inner housing 106. Any seeping gel may be wiped clean with a swab.

FIG. 7 shows a pen 204 used for tracing a reference line on head 90 around as much of perimeter 218 as possible. The z setting of TNS 100 may be recorded on a patient identification card. For example, a location of the top end of threaded ring 146 with respect to gradations 150 on top end 144 of transducer lid 170 may serve as the z reference location (see FIG. 3). The reference line traced around perimeter 218 of inner housing 106 may serve as the x and y reference locations.

An initial ultrasonic treatment then may be applied to patient 88 using TNS 100. After completion of the treatment session, TNS 100 may be wiped clean and placed back into a case. The same TNS 100 may be reserved for all subsequent ultrasonic treatments for the same patient.

Subsequent Alignments and Treatments

Reference marks 216, reference line 214 shown in FIG. 6, and the addition reference line drawn around perimeter 218 of inner housing 106 on head 90, may be visually inspected. Any faded reference marks or lines may be redrawn on head 90.

TNS 100 is adjusted to nominal x and y positions by setting side adjustment knobs 122 each to 6 mm. Gel is again applied to the entire surface of membrane 138. Perimeter 218 of inner housing 106 is concentrically aligned as closely as possible with the reference line that was previously traced around perimeter 218. Housing arm 112 in FIG. 7 is also aligned between the reference lines 214. Outer housing 104 extends down about half an inch over inner housing 106, but still allows viewing of outside perimeter 218 of inner housing 106.

TNS 100 is held firmly against head 90 to prevent it from moving while straps 108 is again wrapped and tightened around head 90. If necessary, elevating screws 122 are rotated down from the position shown in FIG. 8 to the position shown in FIG. 9 to raise inner housing 106 enough to slide over head 90 without moving outer housing 104. As mentioned above, the gel on membrane 138 may maintain a contact layer between membrane 139 and head 90 as inner housing 106 is being adjusted in the x and y positions. The elevating screws reduce pressure of membrane 138 against head 90 of patient 88 and allow membrane 138 to remain in contact against head 90 while inner housing 106 is moved into different x and y positions.

The x and/or y positions of inner housing 106 are adjusted until perimeter 218 visually aligns with the circular marked line previously traced around perimeter 218 as shown in FIG. 7. Elevating screws 122 are rotated upward as shown in FIG. 8 until they no longer touch head 90. The z location of inner housing 106 is verified by comparing the z setting on gradation 150 (FIG. 3) with the z setting on the patient identification card. If necessary, top adjustment knob 142 may be rotated to establish the previous z setting on gradation 150.

An ultrasonic treatment may now begin without having to realign transducer 166 using an MRI device. When the ultrasonic treatment is complete, TNS 100 can be wiped clean and placed back into the original case for the next use by patient 88.

TNS 100 is designed to receive a variety of different transducers that can generate ultrasonic energy into the brain or other body parts at a variety of different depths to accommodate a variety of different disorders. For example, TNS 100 may be used for treating psychiatric disorders, such as depression, anxiety, Obsessive-Compulsive Disorder (OCD), bulimia, bipolar disorder, or autism. TNS 100 also may be used to treat a variety of neurological disorders, such as epilepsy, Parkinson's, Alzheimer's, and other dementias, coma, and brain injury. TNS 100 also may be used to treat medical conditions, such as high and low blood pressure, obesity, and endocrine and immunological disease; and perform functional diagnostics of brain circuits.

The system described above can use dedicated processor systems, micro controllers, programmable logic devices, or microprocessors that perform some or all of the operations. Some of the operations described above may be implemented in software, such as computer readable instructions contained on a storage media, or the same or other operations may be implemented in hardware.

For the sake of convenience, the operations are described as various interconnected functional blocks or distinct software modules. This is not necessary, however, and there may be cases where these functional blocks or modules are equivalently aggregated into a single logic device, program or operation with unclear boundaries. In any event, the functional blocks and software modules or features of the flexible interface can be implemented by themselves, or in combination with other operations in either hardware or software.

References above have been made in detail to preferred embodiment. Examples of the preferred embodiments were illustrated in the referenced drawings. While preferred embodiments where described, it should be understood that this is not intended to limit the invention to one preferred embodiment. To the contrary, it is intended to cover alternatives, modifications, and equivalents as may be included within the spirit and scope of the invention as defined by the appended claims.

Having described and illustrated the principles of the invention in a preferred embodiment thereof, it should be apparent that the invention may be modified in arrangement and detail without departing from such principles. Claim is made to all modifications and variation coming within the spirit and scope of the following claims.

The invention claimed is:

1. An apparatus, comprising:
an outer housing configured to attach to a patient;
an inner housing attached to the outer housing;
a transducer retained within the inner housing and having an x-axis, y-axis, and z-axis, wherein the z-axis is substantially transverse to the patient; and
an alignment assembly attaching the inner housing to the outer housing and configured to move the transducer within the inner housing into different positions along the x-axis and y-axis while the outer housing is attached to the patient.

2. The apparatus of claim 1, wherein the outer housing comprises:
arms extending radially outward from side walls; and
elevating screws extending through the arms and configured to each independently press against different locations on the patient and lift the inner and outer housing.

3. The apparatus of claim 2, wherein the alignment assembly further comprises side adjustment assemblies configured to move the transducer within the inner housing into the different positions while the elevating screws lift the inner housing and the outer housing.

4. The apparatus of claim 3, wherein the side adjustment assemblies comprise:
extensions extending from sides of the outer housing; and
adjustment screws threadedly coupled inside of the extensions and configured to push and pull the inner housing.

5. The apparatus of claim 4, wherein the side adjustment assemblies further comprise:
gradations located on an outside surface of the extensions; and
side adjustment knobs attached to ends of the adjustment screws and configured to rotate the adjustment screws and identify on the gradations a distance of movement of the inner housing.

6. The apparatus of claim 4, further comprising pins located on sides of the outer housing opposite the extensions, wherein the pins are slidingly retained inside of holes extending into sides of the inner housing.

7. The apparatus of claim 1, wherein the inner housing further comprises:
a top end configured to slide against the outer housing; and
a bottom end having a flexible membrane configured to press against the patient.

8. The apparatus of claim 1, wherein the inner housing forms an internal chamber for retaining water or oil.

9. The apparatus of claim 8, further comprising nozzles extending through side walls of the inner housing, wherein the nozzles are configured to fill the internal chamber with the water or oil and bleed air bubbles from the internal chamber.

10. The apparatus of claim 1, further comprising a transducer assembly configured to move the transducer within the inner housing in different positions along the z-axis.

11. The apparatus of claim 10, wherein the transducer assembly further comprises:
a transducer lid forming an airtight cavity on a back side the transducer; and
a transducer base coupled to the transducer lid and forming a watertight cavity over a front side of the transducer configured to retain water.

12. The apparatus of claim 11, wherein the transducer assembly further comprises a neck extending up from the transducer lid through the inner housing and the outer housing.

13. The apparatus of claim 12, further comprising a threaded ring extending up through the inner housing and the outer housing and including a threaded inside surface configured to engage with threads formed on an outside surface of the neck.

14. The apparatus of claim 13, further comprising gradations formed on the outside surface of the neck, wherein a position of the threaded ring over the gradations identifies a distance of movement of the transducer.

15. The apparatus of claim 13, further comprising a first O-ring located between the threaded ring and the outside surface of the neck and a second O-ring located between the ring and a top wall of the inner housing.

16. The apparatus of claim 13, further comprising a top adjustment knob located on top of the outer housing and coupled around the threaded ring, the top adjustment knob configured to rotate the threaded ring to control movement of the transducer assembly inside of the inner housing.

17. The apparatus of claim 13, further comprising a cap threadedly coupled into a top end of the neck and extending over the threaded ring.

18. The apparatus of claim 1, further comprising straps configured to hold the outer housing and inner housing to the patient, wherein the outer housing is configured to lift the inner housing over the patient while the straps hold the outer housing to the patient.

19. The apparatus of claim 1, further comprising a flexible membrane coupled to a front face of the inner housing configured to maintain contact against the patient while the inner housing is moved into the different positions.

20. An apparatus, comprising:
    an outer housing configured to attach to a patient;
    an inner housing attached to the outer housing;
    a transducer retained within the inner housing having an x-axis, y-axis, and z-axis, wherein the z-axis is substantially transverse to a surface of the patient; and
    an alignment assembly coupled between the outer housing and the inner housing and configured to move the inner housing and the transducer into different positions along the x-axis and y-axis.

21. The apparatus of claim 20, further comprising a transducer assembly configured to move the transducer into different positions along the z-axis.

22. The apparatus of claim 20, wherein the outer housing comprises:
    arms extending radially out from side walls; and
    elevating screws extending through the arms and configured to independently press against different locations on the patient.

23. The apparatus of claim 20, wherein the alignment assembly includes side adjustment assemblies configured to move the transducer within the inner housing into the different positions.

24. The apparatus of claim 23, wherein the side adjustment assemblies comprise:
    extensions extending radially inwards from inner sides of the outer housing; and
    adjustment screws threadedly coupled inside of the extensions and extending radially inwards and configured to push and pull the inner housing.

25. The apparatus of claim 24, wherein the side adjustment assemblies further comprise:
    gradations located on an outside surface of the extensions; and
    side adjustment knobs attached to ends of the adjustment screws and configured to rotate the adjustment screws and identify on the gradations a distance of movement of the inner housing.

26. The apparatus of claim 24, further comprising pins located on sides of the outer housing extending inwards toward the adjustment screws, wherein the pins are slidingly retained inside of holes extending into sides of the inner housing.

27. The apparatus of claim 20, wherein the inner housing further comprises:
    a top end configured to slide against an inside surface of the outer housing; and
    a bottom end having a flexible membrane configured to press against the patient.

28. A transducer navigation system, comprising:
    an outer housing configured to attach to a patient;
    an inner housing attached to the outer housing;
    a transducer retained within the inner housing having an x-axis, y-axis, and z-axis, wherein the z-axis is substantially transverse to the patient; and
    an alignment assembly coupled between the outer housing and the inner housing and configured to move the transducer in the inner housing into different positions along the x-axis and y-axis.

29. The system of claim 28, further comprising a transducer assembly configured to move the transducer within the inner housing into different positions along the z-axis.

30. The system of claim 28, wherein the outer housing comprises:
    arms extending radially out from side walls; and
    elevating screws extending through the arms and configured to independently press against different locations on the patient.

* * * * *